(12) United States Patent
Bodepudi et al.

(10) Patent No.: US 9,476,091 B2
(45) Date of Patent: *Oct. 25, 2016

(54) USE OF G-CLAMP FOR IMPROVED ALLELE-SPECIFIC PCR

(71) Applicant: Roche Molecular Systems, Inc., Pleasanton, CA (US)

(72) Inventors: Veeraiah Bodepudi, San Ramon, CA (US); Nancy Schoenbrunner, Moraga, CA (US); Alison Tsan, Castro Valley, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 137 days.

This patent is subject to a terminal disclaimer.

(21) Appl. No.: 13/624,077

(22) Filed: Sep. 21, 2012

(65) Prior Publication Data

US 2013/0078630 A1 Mar. 28, 2013

Related U.S. Application Data

(60) Provisional application No. 61/538,650, filed on Sep. 23, 2011.

(51) Int. Cl.
    *C12Q 1/68* (2006.01)
    *C12P 19/34* (2006.01)
    *C07H 21/04* (2006.01)

(52) U.S. Cl.
    CPC .......... *C12Q 1/6858* (2013.01); *C12Q 1/6883* (2013.01); *C12Q 1/6886* (2013.01); *C12Q 2600/156* (2013.01)

(58) Field of Classification Search
None
See application file for complete search history.

(56) References Cited

U.S. PATENT DOCUMENTS 6,361,940 B1 * 3/2002 Van Ness et al. ............ 435/6.12
2009/0181378 A1 7/2009 Sanders et al.

FOREIGN PATENT DOCUMENTS

| CN | 1737162 A | 2/2006 |
|---|---|---|
| WO | 2010046067 A9 | 4/2010 |
| WO | 2012084173 A2 | 6/2012 |
| WO | 2012084173 A3 | 6/2012 |
| WO | PCT/EP2012/003817 | 12/2012 |

OTHER PUBLICATIONS

Latorra et al., "Enhanced Allele-Specific PCR Discrimination in SNP Genotyping Using 3' Locked Nucleic Acid (LNA) Primers," Human Mutation, 2003, vol. 22, pp. 79-85.*
Maheswaran et al., "Detection of Mutations in EGFR in Circulating Lung-Cancer Cells," The New England Journal of Medicine, 2008, vol. 359, pp. 366-377.*
U.S. Appl. No. 14/092,133, filed Nov. 27, 2013.*
U.S. Appl. No. 13/324,705, filed Dec. 13, 2011.*
Cline et al., "PCR fidelity of Pfu DNA polymerase and other thermostable DNA polymerases," Nucleic Acids Research, 1996, vol. 24, No. 18, pp. 3546-3551.*
Levin et al., "Position-dependent effects of locked nucleic acid (LNA) on DNA sequencing and PCR primers," Nucleic Acids Research, 2006, vol. 34, No. 20, e142, pp. 1-11.*
Ortega, Jose-Antonio, et al., 2007, "Binding Affinities of Oligonucleotides and PNAs Containing Phenoxazine and G-Clamp Cytosine Analogues Are Unusually Sequence-Dependent", Organic Letters, 9(22):4503-4506.

* cited by examiner

*Primary Examiner* — Young J Kim
(74) *Attorney, Agent, or Firm* — David J. Chang (57) ABSTRACT

The present invention includes a method of allele-specific amplification, utilizing an allele-specific oligonucleotide, at least partially complementary to more than one variant of the target sequence, but having at least one selective nucleotide complementary to only one variant of the target sequence and incorporating at least one "G-clamp" nucleotide.

9 Claims, 4 Drawing Sheets

```
   1 ATGCGACCCTCCGGGACGGCCGGGGCAGCGCTCCTGGCGCTGCTGGCTGCGCTCTGCCCG
  61 GCGAGTCGGGCTCTGGAGGAAAAGAAAGTTTGCCAAGGCACGAGTAACAAGCTCACGCAG
 121 TTGGGCACTTTTGAAGATCATTTTCTCAGCCTCCAGAGGATGTTCAATAACTGTGAGGTG
 181 GTCCTTGGGAATTTGGAAATTACCTATGTGCAGAGGAATTATGATCTTTCCTTCTTAAAG
 241 ACCATCCAGGAGGTGGCTGGTTATGTCCTCATTGCCCTCAACACAGTGGAGCGAATTCCT
 301 TTGGAAAACCTGCAGATCATCAGAGGAAATATGTACTACGAAAATTCCTATGCCTTAGCA
 361 GTCTTATCTAACTATGATGCAAATAAAACCGGACTGAAGGAGCTGCCCATGAGAAATTTA
 421 CAGGAAATCCTGCATGGCGCCGTGCGGTTCAGCAACAACCCTGCCCTGTGCAACGTGGAG
 481 AGCATCCAGTGGCGGGACATAGTCAGCAGTGACTTTCTCAGCAACATGTCGATGGACTTC
 541 CAGAACCACCTGGGCAGCTGCCAAAAGTGTGATCCAAGCTGTCCCAATGGGAGCTGCTGG
 601 GGTGCAGGAGAGGAGAACTGCCAGAAACTGACCAAAATCATCTGTGCCCAGCAGTGCTCC
 661 GGGCGCTGCCGTGGCAAGTCCCCCAGTGACTGCTGCCACAACCAGTGTGCTGCAGGCTGC
 721 ACAGGCCCCCGGGAGAGCGACTGCCTGGTCTGCCGCAAATTCCGAGACGAAGCCACGTGC
 781 AAGGACACCTGCCCCCCACTCATGCTCTACAACCCCACCACGTACCAGATGGATGTGAAC
 841 CCCGAGGGCAAATACAGCTTTGGTGCCACCTGCGTGAAGAAGTGTCCCCGTAATTATGTG
 901 GTGACAGATCACGGCTCGTGCGTCCGAGCCTGTGGGCCGACAGCTATGAGATGGAGGAA
 961 GACGGCGTCCGCAAGTGTAAGAAGTGCGAAGGGCCTTGCCGCAAAGTGTGTAACGGAATA
1021 GGTATTGGTGAATTTAAAGACTCACTCTCCATAAATGCTACGAATATTAAACACTTCAAA
1081 AACTGCACCTCCATCAGTGGCGATCTCCACATCCTGCCGGTGGCATTTAGGGGTGACTCC
1141 TTCACACATACTCCTCCTCTGGATCCACAGGAACTGGATATTCTGAAAACCGTAAAGGAA
1201 ATCACAGGGTTTTTGCTGATTCAGGCTTGGCCTGAAAACAGGACGGACCTCCATGCCTTT
1261 GAGAACCTAGAAATCATACGCGGCAGGACCAAGCAACATGGTCAGTTTTCTCTTGCAGTC
1321 GTCAGCCTGAACATAACATCCTTGGGATTACGCTCCCTCAAGGAGATAAGTGATGGAGAT
1381 GTGATAATTTCAGGAAACAAAAATTTGTGCTATGCAAATACAATAAACTGGAAAAAACTG
1441 TTTGGGACCTCCGGTCAGAAAACCAAAATTATAAGCAACAGAGGTGAAAACAGCTGCAAG
1501 GCCACAGGCCAGGTCTGCCATGCCTTGTGCTCCCCCGAGGGCTGCTGGGGCCCGGAGCCC
1561 AGGGACTGCGTCTCTTGCCGGAATGTCAGCCGAGGCAGGGAATGCGTGGACAAGTGCAAC
```

FIGURE 2B

```
1621 CTTCTGGAGGGTGAGCCAAGGGAGTTTGTGGAGAACTCTGAGTGCATACAGTGCCACCCA
1681 GAGTGCCTGCCTCAGGCCATGAACATCACCTGCACAGGACGGGGACCAGACAACTGTATC
1741 CAGTGTGCCCACTACATTGACGGCCCCCACTGCGTCAAGACCTGCCCGGCAGGAGTCATG
1801 GGAGAAAACAACACCCTGGTCTGGAAGTACGCAGACGCCGGCCATGTGTGCCACCTGTGC
1861 CATCCAAACTGCACCTACGGATGCACTGGGCCAGGTCTTGAAGGCTGTCCAACGAATGGG
1921 CCTAAGATCCCGTCCATCGCCACTGGGATGGTGGGGCCCTCCTCTTGCTGCTGGTGGTG
1981 GCCCTGGGGATCGGCCTCTTCATGCGAAGGCGCCACATCGTTCGGAAGCGCACGCTGCGG
2041 AGGCTGCTGCAGGAGAGGGAGCTTGTGGAGCCTCTTACACCCAGTGGAGAAGCTCCCAAC
2101 CAAGCTCTCTTGAGGATCTTGAAGGAAACTGAATTCAAAAAGATCAAAGTGCTGGGCTCC
2161 GGTGCGTTCGGCACGGTGTATAAGGGACTCTGGATCCCAGAAGGTGAGAAAGTTAAAATT
2221 CCCGTCGCTATCAAGGAATTAAGAGAAGCAACATCTCCGAAAGCCAACAAGGAAATCCTC
2281 GATGAAGCCTACGTGATGGCCAGCGTGGACAACCCCCACGTGTGCCGCCTGCTGGGCATC
2341 TGCCTCACCTCCACCGTGCAGCTCATCACGCAGCTCATGCCCTTCGGCTGCCTCCTGGAC
2401 TATGTCCGGGAACACAAAGACAATATTGGCTCCCAGTACCTGCTCAACTGGTGTGTGCAG
2461 ATCGCAAAGGGCATGAACTACTTGGAGGACCGTCGCTTGGTGCACCGCGACCTGGCAGCC
2521 AGGAACGTACTGGTGAAAACACCGCAGCATGTCAAGATCACAGATTTTGGGCTGGCCAAA
2581 CTGCTGGGTGCGGAAGAGAAAGAATACCATGCAGAAGGAGGCAAAGTGCCTATCAAGTGG
2641 ATGGCATTGGAATCAATTTTACACAGAATCTATACCCACCAGAGTGATGTCTGGAGCTAC
2701 GGGGTGACTGTTTGGGAGTTGATGACCTTTGGATCCAAGCCATATGACGGAATCCCTGCC
2761 AGCGAGATCTCCTCCATCCTGGAGAAAGGAGAACGCCTCCCTCAGCCACCCATATGTACC
2821 ATCGATGTCTACATGATCATGGTCAAGTGCTGGATGATAGACGCAGATAGTCGCCCAAAG
2881 TTCCGTGAGTTGATCATCGAATTCTCCAAAATGGCCCGAGACCCCCAGCGCTACCTTGTC
2941 ATTCAGGGGGATGAAAGAATGCATTTGCCAAGTCCTACAGACTCCAACTTCTACCGTGCC
3001 CTGATGGATGAAGAAGACATGGACGACGTGGTGGATGCCGACGAGTACCTCATCCCACAG
3061 CAGGGCTTCTTCAGCAGCCCCTCCACGTCACGGACTCCCCTCCTGAGCTCTCTGAGTGCA
3121 ACCAGCAACAATTCCACCGTGGCTTGCATTGATAGAAATGGGCTGCAAAGCTGTCCCATC
3181 AAGGAAGACAGCTTCTTGCAGCGATACAGCTCAGACCCCACAGGCGCCTTGACTGAGGAC
```

FIGURE 2C

3241 AGCATAGACGACACCTTCCTCCCAGTGCCTGAATACATAAACCAGTCCGTTCCCAAAAGG

3301 CCCGCTGGCTCTGTGCAGAATCCTGTCTATCACAATCAGCCTCTGAACCCCGCGCCCAGC

3361 AGAGACCCACACTACCAGGACCCCCACAGCACTGCAGTGGGCAACCCCGAGTATCTCAAC

3421 ACTGTCCAGCCCACCTGTGTCAACAGCACATTCGACAGCCCTGCCCACTGGGCCCAGAAA

3481 GGCAGCCACCAAATTAGCCTGGACAACCCTGACTACCAGCAGGACTTCTTTCCCAAGGAA

3541 GCCAAGCCAAATGGCATCTTTAAGGGCTCCACAGCTGAAAATGCAGAATACCTAAGGGTC

3601 GCGCCACAAAGCAGTGAATTTATTGGAGCATGA

USE OF G-CLAMP FOR IMPROVED ALLELE-SPECIFIC PCR

CROSS REFERENCE TO RELATED INVENTION

This application claims the benefit of priority of U.S. Provisional Patent Application Ser. No. 61/538,650, filed Sep. 23, 2011, which is incorporated herein by reference in its entirety.

REFERENCE TO SEQUENCE LISTING

This application contains a Sequence Listing submitted as an electronic text file named "27369_US1_Sequence_Listing.txt", having a size in bytes of 14 kb, and created on Sep. 14, 2012. The information contained in this electronic file is hereby incorporated by reference in its entirety pursuant to 37 CFR §1.52(e)(5).

FIELD OF THE INVENTION

The invention relates to the field of nucleic acid amplification and specifically, to the field of allele-specific amplification.

BACKGROUND OF THE INVENTION

Allele-specific amplification of nucleic acids allows for simultaneous amplification and analysis of the target sequence. Allele-specific amplification is commonly used when the target nucleic acid is suspected of having one or more subpopulations with a variation (polymorphism) in its sequence. DNA polymorphisms are used in DNA profile analysis (forensics, paternity testing, tissue typing for organ transplants), genetic mapping, as well as detection of rare mutations, such as those occurring in cancer cells in the background of cells with normal DNA.

In a successful allele-specific amplification, the desired variant of the target nucleic acid is amplified, while the other variants are not, at least not to a detectable level. A typical allele-specific amplification assay involves a polymerase chain reaction (PCR) where at least one primer is complementary to the region with a suspected polymorphism. The design of the allele-specific primer is such that primer extension occurs only when a certain variant of the polymorphism is present. In its simplest form, the allele-specific primer has a 3'-terminal nucleotide complementary to the desired variant of the polymorphic nucleotide in the target. Often a single mismatch at the 3'-terminus of the primer is sufficient to preclude amplification of the undesired variants of the target sequence. However, specificity of amplification varies greatly among different 3'-terminal sequences: some mismatches effectively block extension by the polymerase, while others do not, see U.S. Pat. No. 5,639,611.

The success of allelic discrimination depends on the inability of the DNA polymerase to extend mismatched primers. This inability of the DNA polymerase may be modulated by adjusting the reaction conditions to achieve maximum selectivity. Nevertheless, poor selectivity of allele-specific PCR remains a problem for many polymorphic sequences.

One approach to increasing specificity involves engineering amplification primers with an internal mismatched nucleotide or nucleotides. This approach proved successful in some systems, see U.S. Pat. No. 5,137,806.

Another approach to increasing specificity involves chemical modification of the primers. For example, it was found that certain 2'-C and 4'-C modifications of the deoxyribose of some nucleotides in the primer enhance allele discrimination by the polymerase. See Gaster, J. and Marx, A., Chem. Eur. J. 2005, 11:1861-1870. In another study, it was found that allelic discrimination is enhanced by the use of an unnatural pyrimidine base in one of the nucleotides in the primer, specifically, pseudoisocytidine with various substituents in the 6-position of the pyrimidine ring, see U.S. Pat. No. 7,408,051.

In the context of real-time allele-specific PCR, the selectivity of the assay may be measured as the difference in the threshold cycle number (Ct) between the matched and mismatched templates. A greater difference indicates a greater delay in amplification of the mismatched template and thus a greater discrimination between alleles. The modified deoxyribose has been shown to result in Ct differences of between 1 and 14 cycles. The use of pseudoisocytidine resulted in a 7-cycle delay in amplification of the mismatched template. This degree of discrimination is insufficient for many applications, where the sample contains several variants of the template, all competing for amplification. Often the mismatched template is present in much greater amounts than the matched template. For example, in tissue samples, only a small fraction of cells may be malignant and carry the mutation ("matched template"), targeted by the allele-specific amplification assay. The template present in normal cells may be amplified less efficiently, but the overwhelming numbers of normal cells will overcome any delay in amplification and erase any advantage of the mutant template. To detect rare mutations in the presence of the wild-type template, the specificity of the allele-specific amplification assay needs to be improved.

Many ways of enhancing allele-specificity of primers have been proposed. However, for many clinically-relevant nucleic acid targets, the lack of specificity of PCR remains a problem. Therefore, novel approaches to the design of allele-specific primers are necessary.

Figure 1:
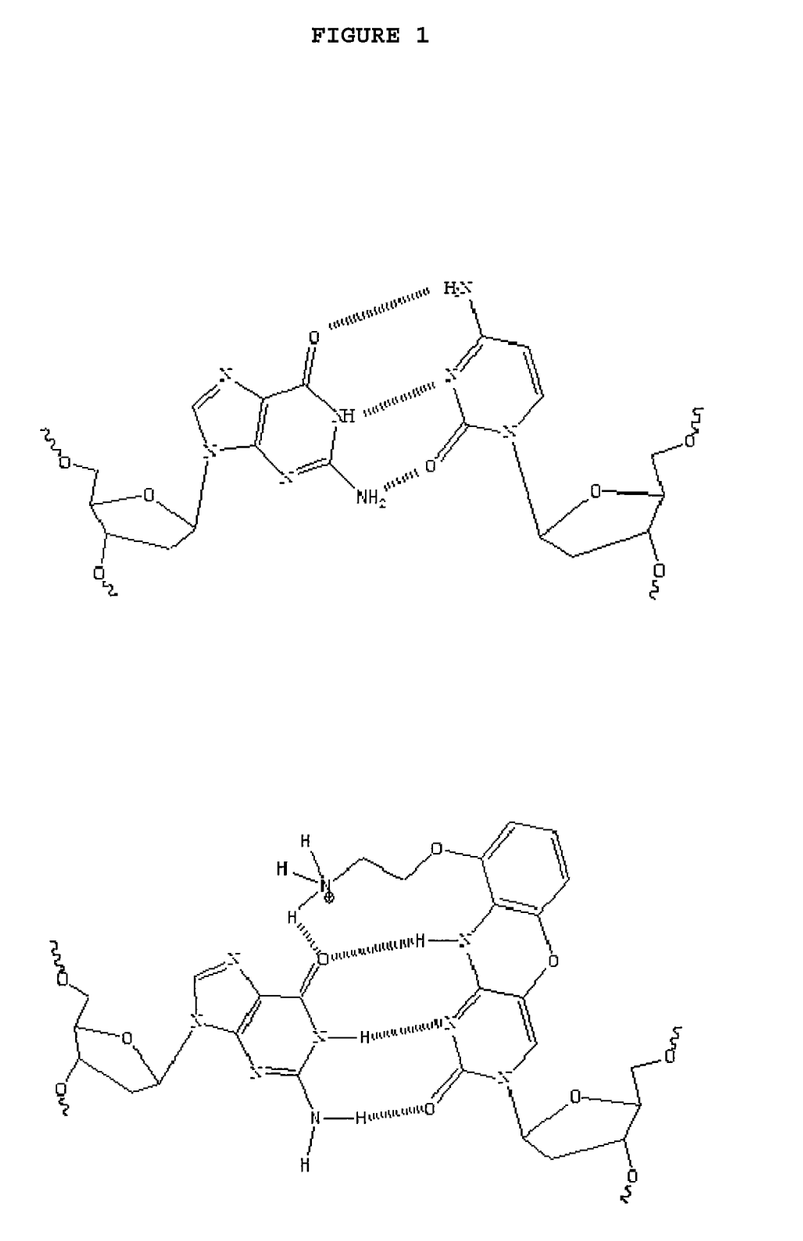
FIG. 1 shows the hydrogen bond interaction between deoxyguanine and deoxycytidine (top) and between deoxyguanine and G-clamp (bottom).

The G-clamp is a tricyclic aminoethoxy-phenoxazine-2'-deoxycytidine, which is a cytosine analogue, shown in FIG. 1. G-clamp, when incorporated into oligonucleotides, simultaneously recognizes both the Watson-Crick and Hoogsteen faces of a complementary guanine within a helix. Hence G-clamp containing oligonucleotides substantially enhanced helical thermal stability and mismatch discrimination when hybridized to complementary DNA and RNA strands. These properties of enhanced affinity and specificity are of interest in the fields of nucleic acid based diagnostics and the sequence-specific targeting of RNA by the antisense approach. Further features of G-clamp and related pyrimidine derivatives are disclosed in U.S. Pat. Nos. 6,414,127, 6,951,931, 7,511,125 and U.S. Pat. No. RE39,324.

SUMMARY OF THE INVENTION

In a first aspect, the invention relates to a method of allele-specific amplification of a variant of a target sequence, the target existing in the form of several variant sequences, the method comprising (a) hybridizing a first and a second oligonucleotides to at least one variant of the target sequence; wherein the first oligonucleotide is at least partially complementary to one or more variants of the target sequence, and the second oligonucleotide is at least partially complementary to one or more variants of the target sequence, and has at least one selective nucleotide complementary to only one variant of the target sequence; wherein the second oligonucleotide incorporates at least one "G-clamp" nucleotide; (b) extending the second oligonucleotide with a nucleic acid polymerase, wherein the polymerase is capable of extending the second oligonucleotide efficiently when the second oligonucleotide is hybridized to a variant of the target sequence which is complementary to the at least one selective nucleotide, and substantially less efficiently when the second oligonucleotide is hybridized to a variant of the target sequence which is not complementary to the at least one selective nucleotide.

In a second aspect, the invention relates to a kit for allele-specific amplification of a target sequence, the target existing in the form of several variant sequences, the kit comprising: (a) a first oligonucleotide, at least partially complementary to one or more variant of the target sequence; and (b) a second oligonucleotide, at least partially complementary to one or more variants of the target sequence having at least one selective nucleotide complementary to only one variant of the target sequence, wherein the second oligonucleotide incorporates at least one "G-clamp" nucleotide.

In a third aspect, the invention relates to an oligonucleotide for performing an allele-specific amplification of a target sequence, the target existing in the form of several variant sequences, the oligonucleotide comprising (a) a sequence at least partially complementary to a portion of one or more variants of said target sequence; (b) at least one selective nucleotide complementary to only one variant of the target sequence; (c) at least one "G-clamp" nucleotide.

In a fourth aspect, the invention relates to a reaction mixture for allele-specific amplification of a target sequence, the target existing in the form of several variant sequences, the mixture comprising: (a) a first oligonucleotide, at least partially complementary to one or more variant of the target sequence; and (b) a second oligonucleotide, at least partially complementary to one or more variants of the target sequence but having at least one selective nucleotide complementary to only one variant of the target sequence; wherein said second oligonucleotide incorporates at least one "G-clamp" nucleotide.

BRIEF DESCRIPTION OF THE DRAWINGS

FIG. 2(A-C) shows the coding sequence of the wild-type human EGFR gene (SEQ ID NO: 1).

DETAILED DESCRIPTION OF THE INVENTION

Definitions

Unless defined otherwise, all technical and scientific terms used herein have the same meaning as commonly understood by one of ordinary skill in the art to which this invention pertains. In describing and claiming the present invention, the following definitions will be used.

The term "nucleic acid" refers to polymers of nucleotides (e.g., ribonucleotides, deoxyribonucleotides, nucleotide analogs etc.) and comprising deoxyribonucleic acids (DNA), ribonucleic acids (RNA), DNA-RNA hybrids, oligonucleotides, polynucleotides, aptamers, peptide nucleic acids (PNAs), PNA-DNA conjugates, PNA-RNA conjugates, etc., that comprise nucleotides covalently linked together, either in a linear or branched fashion. A nucleic acid is typically single-stranded or double-stranded and will generally contain phosphodiester bonds, although in some cases, nucleic acid analogs are included that may have alternate backbones, including, for example, phosphoramide (Beaucage et al. (1993) Tetrahedron 49(10):1925); phosphorothioate (Mag et al. (1991) Nucleic Acids Res. 19:1437; and U.S. Pat. No. 5,644,048), phosphorodithioate (Briu et al. (1989) J. Am. Chem. Soc. 111:2321), O-methylphophoroamidite linkages (see Eckstein, Oligonucleotides and Analogues: A Practical Approach, Oxford University Press (1992)), and peptide nucleic acid backbones and linkages (see, Egholm (1992) J. Am. Chem. Soc. 114:1895). Other analog nucleic acids include those with positively charged backbones (Denpcy et al. (1995) Proc. Natl. Acad. Sci. USA 92: 6097); non-ionic backbones (U.S. Pat. Nos. 5,386,023, 5,637,684, 5,602,240, 5,216,141 and 4,469,863) and non-ribose backbones, including those described in U.S. Pat. Nos. 5,235,033 and 5,034,506. Nucleic acids containing one or more carbocyclic sugars are also included within the definition of nucleic acids (see Jenkins et al. (1995) Chem. Soc. Rev. pp. 169-176), and analogs are also described in, e.g., Rawls, C & E News Jun. 2, 1997 page 35. These modifications of the ribose-phosphate backbone may be done to facilitate the addition of additional moieties such as labels, or to alter the stability and half-life of such molecules in physiological environments.

In addition to the naturally occurring heterocyclic bases that are typically found in nucleic acids (e.g., adenine, guanine, thymine, cytosine, and uracil), nucleotide analogs also may include non-naturally occurring heterocyclic bases, such as those described in, e.g., Seela et al. (1999) Hely. Chim. Acta 82:1640. Certain bases used in nucleotide analogs act as melting temperature (Tm) modifiers. For example, some of these include 7-deazapurines (e.g., 7-deazaguanine, 7-deazaadenine, etc.), pyrazolo[3,4-d]pyrimidines, propynyl-dN (e.g., propynyl-dU, propynyl-dC, etc.), and the like. See, e.g., U.S. Pat. No. 5,990,303, which is incorporated herein by reference. Other representative heterocyclic bases include, e.g., hypoxanthine, inosine, xanthine; 8-aza derivatives of 2-aminopurine, 2,6-diaminopurine, 2-amino-6-chloropurine, hypoxanthine, inosine and xanthine; 7-deaza-8-aza derivatives of adenine, guanine, 2-aminopurine, 2,6-diaminopurine, 2-amino-6-chloropurine, hypoxanthine, inosine and xanthine; 6-azacytidine; 5-fluorocytidine; 5-chlorocytidine; 5-iodocytidine; 5-bromocytidine; 5-methylcytidine; 5-propynylcytidine; 5-bromovinyluracil; 5-fluorouracil; 5-chlorouracil; 5-iodouracil; 5-bromouracil; 5-trifluoromethyluracil; 5-methoxymethyluracil; 5-ethynyluracil; 5-propynyluracil, and the like.

A "nucleoside" refers to a nucleic acid component that comprises a base or basic group (comprising at least one homocyclic ring, at least one heterocyclic ring, at least one aryl group, and/or the like) covalently linked to a sugar moiety (a ribose sugar or a deoxyribose sugar), a derivative of a sugar moiety, or a functional equivalent of a sugar moiety (e.g. a carbocyclic ring). For example, when a nucleoside includes a sugar moiety, the base is typically linked to a 1'-position of that sugar moiety. As described above, a base can be a naturally occurring base or a non-naturally occurring base. Exemplary nucleosides include ribonucleosides, deoxyribonucleosides, dideoxyribonucleosides and carbocyclic nucleosides.

A "nucleotide" refers to an ester of a nucleoside, e.g., a phosphate ester of a nucleoside, having one, two, three or more phosphate groups covalently linked to a 5' position of a sugar moiety of the nucleoside.

A "purine nucleotide" refers to a nucleotide that comprises a purine base, whereas a "pyrimidine nucleotide" refers to a nucleotide that comprises a pyrimidine base.

A "G-clamp" nucleotide refers to the cytosine analogue, 9-(aminoethoxy)-phenoxazine-2'-deoxycytidine and is disclosed in U.S. Pat. No. 6,414,127, which is incorporated by reference in its entirety.

An "oligonucleotide" refers to a nucleic acid polymer that includes at least two, but typically 5-50 nucleotides and more typically, between 15 and 35 nucleotides. The exact size of an oligonucleotide generally depends on various factors, including the ultimate function or use of the oligonucleotide. Oligonucleotides may be prepared by any suitable method known in the art, including, for example, cloning and restriction digestion of appropriate sequences, or direct chemical synthesis by a method such as the phosphotriester method of Narang et al. (1979) Meth. Enzymol. 68:90-99; the phosphodiester method of Brown et al. (1979) Meth. Enzymol. 68:109-151; the diethylphosphoramidite method of Beaucage et al. (1981) Tetrahedron Lett. 22:1859-1862; the triester method of Matteucci et al. (1981) J. Am. Chem. Soc. 103:3185-3191; automated synthesis methods; the solid support method of U.S. Pat. No. 4,458,066 or any other chemical method known in the art.

A "primer nucleic acid" or "primer" is an oligonucleotide that can hybridize to a template nucleic acid and permit chain extension or elongation using a nucleotide incorporating biocatalyst. Although other primer lengths are sometimes utilized, primers typically range from 15 to 35 nucleotides. Short primer nucleic acids generally utilize cooler temperatures to form sufficiently stable hybrid complexes with template nucleic acids. A primer nucleic acid that is at least partially complementary to a subsequence of a template nucleic acid is typically sufficient to hybridize with the template nucleic acid for extension to occur. However, the success of the extension generally requires greater complementarity (i.e. fewer mismatches with the template) at the 3'-end of the primer. A primer nucleic acid can be labeled, if desired, by incorporating a label detectable by radiological, spectroscopic, photochemical, biochemical, immunochemical, or chemical techniques.

An "extended primer" refers to a primer to which one or more additional nucleotides have been added. "Primer extension" is the action of the enzyme by which additional nucleotides are added to the primer.

A "template nucleic acid", "template" or "target" refers to a nucleic acid to which a primer nucleic acid can hybridize and be extended under suitable conditions. In the context of nucleic acid amplification, "target" is preferably a region of double stranded nucleic acid, consisting of the sequences at least partially complementary to at least two primer sequences and the intervening sequence. A target can also be a single stranded nucleic acid, consisting of a sequence at least partially complementary to one primer and a sequence partially identical to the second primer. Template nucleic acids can exist as isolated nucleic acid fragments or be a part of a larger nucleic acid fragment. Target nucleic acids can be derived or isolated from essentially any source, such as cultured microorganisms, uncultured microorganisms, complex biological mixtures, tissues, sera, ancient or preserved tissues or samples, environmental isolates or the like. Further, template nucleic acids optionally include or are derived from cDNA, RNA, genomic DNA, cloned genomic DNA, genomic DNA libraries, enzymatically fragmented DNA or RNA, chemically fragmented DNA or RNA, physically fragmented DNA or RNA, or the like. Template nucleic acids can also be chemically synthesized using techniques known in the art.

As used herein, a "gene" refers to any segment of DNA associated with a biological function. Thus, genes include coding sequences and optionally, the regulatory sequences required for the expression of the coding sequences. Nucleic acids are "extended" or "elongated" when additional nucleotides are incorporated into the nucleic acids, for example by a nucleotide incorporating biocatalyst, at the 3' end of a nucleic acid.

A "moiety" or "group" refers to one of the portions into which something, such as a molecule, is divided (e.g., a functional group, substituent group, or the like). For example, a nucleotide typically comprises a base group (e.g., adenine, thymine, cytosine, guanine, uracil, or an analog), a sugar moiety, and one or more phosphate groups.

An "allele-specific primer" is a primer that can hybridize to several variants of the template nucleic acid, but permit elongation by the polymerase when hybridized with only some of the variants of the template nucleic acid. With other variants of the template nucleic acid the primer-template hybrid may not be extended or is extended less efficiently by the polymerase.

Nucleic acids are "extended" or "elongated" when additional nucleotides are incorporated into the nucleic acids, for example by a nucleotide incorporating biocatalyst, at the 3' end of a nucleic acid.

An amplification assay is "selective" or "allele-selective" if it yields predominance (i.e., a majority but less than 100%) of one product over other possible products. An assay is described as "allele-selective" as long as amplification of the undesired (mismatched) variant of the target sequence is detectable. The term "specific" or "allele-specific" with respect to amplification assay is used if one of the possible products is formed exclusively. An assay where amplification of the undesired target is undetectable is called "allele-specific." However, it is understood that as the methods of detection become more sensitive, some assays previously known to be allele-specific, turn out to be allele-selective, i.e. some amplification of undesired variants of the target becomes detectable. Therefore, in the context of this invention, the term "allele-specific" is meant to encompass both strictly allele-specific, as well as allele-selective amplification.

A "genotype" refers to all or part of the genetic constitution of a cell or subject, or group of cells or subjects. For example, a genotype includes the particular mutations and/or alleles (e.g., polymorphisms, such as single nucleotide polymorphisms (SNPs) or the like) present at a given locus or distributed in a genome.

A "nucleic acid polymerase" refers to an enzyme that catalyzes the incorporation of nucleotides into a nucleic acid. Exemplary nucleic acid polymerases include DNA polymerases, RNA polymerases, terminal transferases, reverse transcriptases, telomerases and the like.

A "thermostable enzyme" refers to an enzyme that is stable (i.e., resists breakdown or denaturation) and retains sufficient catalytic activity when subjected to elevated temperatures for selected periods of time. For example, a thermostable polymerase retains sufficient activity to effect subsequent primer extension reactions, when subjected to elevated temperatures for the time necessary to denature double-stranded nucleic acids. Heating conditions necessary for nucleic acid denaturation are well known in the art and are exemplified in U.S. Pat. Nos. 4,683,202 and 4,683,195. As used herein, a thermostable polymerase is typically suitable for use in a temperature cycling reaction such as the polymerase chain reaction ("PCR"). The examples of thermostable nucleic acid polymerases include *Thermus aquaticus* Taq DNA polymerase, *Thermus* sp. Z05 polymerase, *Thermus flavus* polymerase, *Thermotoga maritima* polymerases, such as TMA-25 and TMA-30 polymerases, Tth DNA polymerase, and the like.

A "modified" enzyme refers to an enzyme comprising an amino acid polymer in which at least one monomer differs from the reference sequence, such as a native or wild-type form of the enzyme or another modified form of the enzyme. Exemplary modifications include monomer insertions, deletions, and substitutions. Modified enzymes also include chimeric enzymes that have identifiable component sequences (e.g., structural or functional domains, etc.) derived from two or more parents. Also included within the definition of modified enzymes are those comprising chemical modifications of the reference sequence. The examples of modified polymerases include G46E E678G CS5 DNA polymerase, G46E L329A E678G CS5 DNA polymerase, G46E L329A D640G S671F CS5 DNA polymerase, G46E L329A D640G S671F E678G CS5 DNA polymerase, a G46E E678G CS6 DNA polymerase, Z05 DNA polymerase, ΔZ05 polymerase, ΔZ05-Gold polymerase, ΔZ05R polymerase, E615G Taq DNA polymerase, E678G TMA-25 polymerase, E678G TMA-30 polymerase, and the like.

The term "5' to 3' nuclease activity" or "5'-3' nuclease activity" refers to an activity of a nucleic acid polymerase, typically associated with the nucleic acid strand synthesis, whereby nucleotides are removed from the 5' end of nucleic acid strand, e.g., *E. coli* DNA polymerase I has this activity, whereas the Klenow fragment does not.

A polymerase that "substantially lacks 5'-3' nuclease activity" refers to a polymerase that has 50% or less (e.g., <25%, <20%, <15%, <10%) 5'-3' nuclease activity than Taq DNA polymerase. Methods of measuring 5'-3' nuclease activity and conditions for measurement are well known in the art. See, e.g., U.S. Pat. No. 5,466,591. Examples of DNA polymerases substantially lacking 5' to 3' nuclease activity include the Klenow fragment of *E. coli* DNA polymerase I; a *Thermus aquaticus* DNA polymerase (Taq) lacking the N-terminal 235 amino acids (e.g., as described in U.S. Pat. No. 5,616,494 and commonly referred to in the art as the "Stoffel fragment"). Other examples include a thermostable DNA polymerase having sufficient deletions (e.g., N-terminal deletions), mutations, or modifications so as to eliminate or inactivate the domain responsible for the 5'-3' nuclease activity. See, e.g., U.S. Pat. No. 5,795,762.

The term "3' to 5' nuclease activity" or "3'-5' nuclease activity" or "proof-reading activity" refers to an activity of a nucleic acid polymerase, whereby nucleotides are removed from the 3' end of the nucleic acid strand. For example, *E. coli* DNA polymerase III has this activity, whereas the *Thermus aquaticus* (Taq) DNA polymerase does not.

A "fidelity" or "replication fidelity" is the ability of a nucleic acid polymerase to incorporate a correct nucleotide during template-dependent polymerization. In the context of replication fidelity, "correct nucleotide" on the nascent nucleotide strand is the nucleotide paired with the template nucleotide via Watson-Crick base pairing. Replication fidelity of a particular polymerase results from a combination of incorporating correct nucleotides and removing incorrect nucleotides from the 3'-terminus of the nascent nucleotide strand via the 3'-5' nuclease activity of the polymerase. Various methods of measuring fidelity of a nucleotide polymerase are reviewed in Tindall et al. (1988) Fidelity of DNA synthesis by the *Thermus aquaticus* DNA polymerase. Biochemistry, 27:6008-6013. Typically, polymerases with 3'-5' nuclease (proofreading) capability have higher fidelity than polymerases without the proof-reading activity.

A "label" refers to a moiety attached (covalently or non-covalently), to a molecule and capable of providing information about the molecule. Exemplary labels include fluorescent labels, colorimetric labels, chemiluminescent labels, bioluminescent labels, radioactive labels, mass-modifying groups, antibodies, antigens, biotin, haptens, and enzymes (including peroxidase, phosphatase, etc.).

A "hot start", in the context of a nucleic acid amplification reaction, refers to a protocol, where at least one critical reagent is withheld from the reaction mixture (or, if present in the reaction mixture, the reagent remains inactive) until the temperature is raised sufficiently to provide the necessary hybridization specificity of the primer or primers. A "hot start enzyme" is an enzyme, typically a nucleic acid polymerase, capable of acting as the "withheld" or inactive reagent in a hot start protocol.

A "Watson-Crick base pairing" or simply "base pairing" refers to "conventional" hydrogen bonding within a double-stranded nucleic acid molecule. Watson-Crick base pairing is hyrdrogen bonding between adenine and thymine, between guanine and cytosine, between adenine and uracil, and between analogs of these bases.

A "selective nucleotide" is a nucleotide in an allele-specific primer that confers allele selectivity to the primer. The selective nucleotide is complementary to a corresponding nucleotide in the desired variant of the target nucleic acids but not complementary to the corresponding nucleotide in the undesired variants of the target nucleic acid. In a primer, more than one nucleotide may be complementary to a nucleotide in the desired variants of the target nucleic acids but not complementary to the corresponding nucleotide in the undesired variants of the target nucleic acid. However, the selective nucleotide is located at a position within the primer that affects the specificity of the primer. The selective nucleotide permits efficient or inefficient amplification of the target nucleic acid, depending on whether or not it finds or does not find a complementary partner in the target nucleic acid. A primer may contain more than one selective nucleotide.

The expression "wherein said polymerase is capable of extending said second oligonucleotide efficiently when said second oligonucleotide is hybridized to a variant of the target sequence which is complementary to the at least one selective nucleotide, and substantially less efficiently when said second oligonucleotide is hybridized to a variant of the target sequence which is not complementary to the at least one selective nucleotide." means that extension of the second oligonucleotide by the polymerase is more efficient when the selective nucleotide forms a base pair with the target, than when said selective nucleotide does not form a base pair with the target.

As mentioned above, in one aspect, the present invention relates to a method of allele-specific amplification, comprising (a) providing a sample, possibly containing at least one variant of a target sequence; (b) providing a first oligonucleotide, at least partially complementary to more than one variant of the target sequence; (c) providing a second oligonucleotide, at least partially complementary to one or more variants of the target sequence, having a selective nucleotide complementary to only one variant of the target sequence; wherein said second oligonucleotide incorporates at least one "G-clamp" nucleotide; (d) providing conditions suitable for the hybridization of said first and second oligonucleotides to at least one variant of the target sequence; (e)

providing conditions suitable for the oligonucleotide extension by a nucleic acid polymerase; wherein said polymerase is capable of extending said second oligonucleotide when it is hybridized to the variant of the target sequence for which it has said complementary selective nucleotide, and substantially less when said second oligonucleotide is hybridized to the variant of the target sequence for which it has a non-complementary selective nucleotide.

The second oligonucleotide, at least partially complementary to one or more variants of the target sequence, having a selective nucleotide complementary to only one variant of the target sequence is referred to as a "selective oligonucleotide," "selective primer," or "allele-selective primer." The selective oligonucleotide of the present invention comprises 10-50, more preferably 15-35 nucleotides, the majority of them complementary to a sequence in more than one variant of the target sequence. The selective nucleotide of the oligonucleotide is complementary to a variant of the target sequence that is to be amplified and not complementary to other variants. In one embodiment, the selective nucleotide is the 3'-terminal nucleotide. The selective oligonucleotide of the present invention includes one or more "G-clamp" nucleotides. In some embodiments, the "G-clamp" nucleotide occurs at the 3'-terminal nucleotide. In other embodiments, the "G-clamp" nucleotide occurs between 1 and 5 nucleotides upstream of the 3'-terminal nucleotide. In other embodiments, the modified-base nucleotide is the 3'-terminal nucleotide. In some embodiments, the "G-clamp" nucleotide occurs both at the 3'-terminus and at least once more, elsewhere within the oligonucleotide.

The allele-specific primer of the present invention may incorporate various aspects of primer design known in the art. For example, the primer may take the form of a unimolecular primer-probe combination termed "scorpion" and described in Whitcombe et al., (1999) Detection of PCR products using self-probing amplicons and fluorescence, Nature Biotech. 17:804-807. The scorpion primer designed according to the present invention incorporates the typical elements of the scorpion, namely a probe portion, a stem loop portion and a primer portion. Further, in a scorpion designed according to the present invention, the primer portion has a 3' end complementary to the variant position. The primer portion in a scorpion designed according to the present invention contains one or more "G-clamp" nucleotides as described herein.

In some embodiments of the invention, the amplification involves the polymerase chain reaction, i.e. repeated cycles of template denaturation, annealing (hybridization) of the oligonucleotide primer to the template, and extension of the primer by the nucleic acid polymerase. In some embodiments, the annealing and extension occur at the same temperature step.

In some embodiments, the amplification reaction involves a hot start protocol. In the context of allele-specific amplification, the selectivity of the allele-specific primers with respect to the mismatched target may be enhanced by the use of a hot start protocol. Many hot start protocols are known in the art, for example, the use of wax, separating the critical reagents from the rest of the reaction mixture (U.S. Pat. No. 5,411,876), the use of a nucleic acid polymerase, reversibly inactivated by an antibody (U.S. Pat. No. 5,338,671), a nucleic acid polymerase reversibly inactivated by an oligonucleotide that is designed to specifically bind its active site (U.S. Pat. No. 5,840,867) or the use of a nucleic acid polymerase with reversible chemical modifications, as described e.g. in U.S. Pat Nos. 5,677,152 and 5,773,528.

In some embodiments of the invention, the allele-specific amplification assay is the real-time PCR assay. In a real-time PCR assay, the measure of amplification is the "cycles to threshold" or Ct value. An earlier Ct value reflect the rapid achievement of the threshold level and thus a more efficient amplification. The later Ct value may reflect inefficient or inhibited amplification. In the context of an allele-specific real-time PCR assay, the difference in Ct values between the matched and the mismatched templates is a measure of the discrimination between the alleles or the selectivity of the assay.

The allele-specific amplification assay may employ any suitable nucleic acid polymerase known in the art. For an allele-specific PCR assay, any thermostable nucleic acid polymerase may be used. It is sometimes desirable to use an enzyme without the proof-reading (3'-5'-exonuclease) activity, such as for example, Taq DNA polymerase. It may also be desirable to use enzymes, substantially or entirely lacking the 5'-3' nuclease activity, such as described in U.S. Pat. No. 5,795,762. One example of such an enzyme is ΔZ05 polymerase. It may sometimes be desirable to have an enzyme with a "hot start" capability, such as the reversibly modified enzymes described in U.S. Pat. Nos. 5,677,152 and 5,773,528. One example of a hot-start enzyme is ΔZ05-Gold polymerase.

Detection of the amplification products may be accomplished by any method known in the art. These methods include the use of labeled primers and probes as well as various nucleic acid-binding dyes. The means of detection may be specific to one variant of the target sequence, or may be generic to all variants of the target sequence or even to all double stranded DNA. The non-specific detection methods may be used where the amplification of the undesired variants of the target is minimal and expected to fall below the detection limit of the method.

The amplification products may be detected after the amplification has been completed, for example, by gel electrophoresis of the unlabeled products and staining of the gel with a nucleic acid-binding dye. Alternatively, the amplification products may carry a radioactive or a chemical label, either by virtue of incorporation during synthesis or by virtue of being the extension products of a labeled primer. After, or during electrophoresis, the labeled amplification products may be detected with suitable radiological or chemical tools known in the art. After electrophoresis, the product may also be detected with a target-specific probe labeled by any one of the methods known in the art. The labeled probe may also be applied to the target without electrophoresis, i.e. in a "dot blot" assay or the like.

In other embodiments, the presence of the amplification product may be detected in a homogeneous assay, i.e. an assay where the nascent product is detected during the cycles of amplification, or at least in the same unopened tube, and no post-amplification handling is required. A homogeneous amplification assay has been described for example, in U.S. Pat. No. 5,210,015. Homogeneous amplification assay using nucleic acid-intercalating dyes has been described for example, in U.S. Pat. Nos. 5,871,908 and 6,569,627. The homogeneous assay may also employ fluorescent probes labeled with two interacting fluorophores, such as "molecular beacon" probes (Tyagi et al., (1996) Nat. Biotechnol., 14:303-308) or fluorescently labeled nuclease probes (Livak et al., (1995) PCR Meth. Appl., 4:357-362). In certain variations of these technologies, an amplification product may also be identified by virtue of its distinctive melting temperature, see U.S. Pat. Nos. 5,871,908 and 6,569,627. The amplification products may also be detected using a unimolecular primer-probe combination termed "scorpion." Whitcombe et al., (1999) Detection of PCR products using self-probing amplicons and fluorescence, *Nature Biotech.* 17:804-807. The primer portion of the scorpion oligonucleotide may be an allele-specific primer designed according to the present invention.

In another aspect, the invention provides a reaction mixture for specifically or selectively amplifying a selected variant of the target sequence, comprising a first oligonucleotide, at least partially complementary to more than one variant of the target sequence, a second oligonucleotide, at least partially complementary to more than one variant of the target sequence, but having a selective nucleotide complementary to only one variant of the target sequence, wherein said second oligonucleotide includes at least one "G-clamp" nucleotide and a target nucleic acid, known to exist in more than one sequence variant. In some embodiments, the reaction mixture further comprises the reagents and solutions generally necessary for the amplification of nucleic acids, including a nucleic acid polymerase, nucleic acid precursors, i.e. nucleoside triphosphates, and organic and inorganic ions, suitable for the support of the activity of the nucleic acid polymerase.

In another aspect, the invention provides kits for conducting allele-specific amplification according to the invention. The kit generally includes assay-specific components as well as components generally required for performing DNA amplification assays. As the assay-specific components, the allele-specific amplification kit of the present invention typically includes a first oligonucleotide, at least partially complementary to one or more variant of the target sequence and a second oligonucleotide, at least partially complementary to more than one variant of the target sequence, having a selective nucleotide complementary to only one variant of the target sequence and also having at least one "G-clamp" nucleotide, and optionally a control nucleic acid sequence comprising an amount of at least one variant of the control target sequence, at least partially complementary to the oligonucleotides enclosed in the kit. In some embodiments, more than one variant of the control nucleic acid sequence may be enclosed. In certain embodiments, among the several variants of the control nucleic acid sequence enclosed in the kit, at least one variant is complementary to the selective nucleotide of the allele-selective oligonucleotide. As the components generally required for nucleic acid amplification, the kit of the present invention typically includes one or more of a nucleic acid polymerase, nucleic acid precursors, such as nucleoside triphosphates (deoxyribonucleoside triphosphates or ribonucleoside triphosphates), optionally, a pyrophosphatase, for minimizing pyrophosphorolysis of nucleic acids, a uracil N-glycosylase (UNG) for protection against carry-over contamination of amplification reactions, pre-made reagents and buffers necessary for the amplification reaction and detection, and a set of instructions for conducting allele-specific amplification of the present invention.

In yet another aspect, the invention provides an oligonucleotide for use in allele-specific PCR. A typical oligonucleotide for use in allele-specific PCR of the present invention comprises 10-50, more preferably 15-35 nucleotides, the majority of them complementary to a sequence in more than one variant of the target sequence. However, the selective nucleotide of the oligonucleotide is complementary to one variant of the target sequence and not complementary to other variants. Further, the oligonucleotide of the present invention includes one or more "G-clamp" nucleotides. In some embodiments, the "G-clamp" nucleotide occurs at the 3'-terminal nucleotide. In other emboidents, the "G-clamp" nucleotide occurs between 1 and 5, or for example 1, 2 or 3 nucleotides upstream of the 3'-terminal nucleotide In some embodiments, the "G-clamp" nucleotide occurs both at the 3'-terminus as well as elsewhere within the oligonucleotide.

The following examples and figures are provided to aid the understanding of the present invention, the true scope of which is set forth in the appended claims. It is understood that modifications can be made in the procedures set forth without departing from the spirit of the invention.

EXAMPLES

Example 1

Primers for Detecting Mutation L858R in the Human EGFR Gene

Figure 2C:
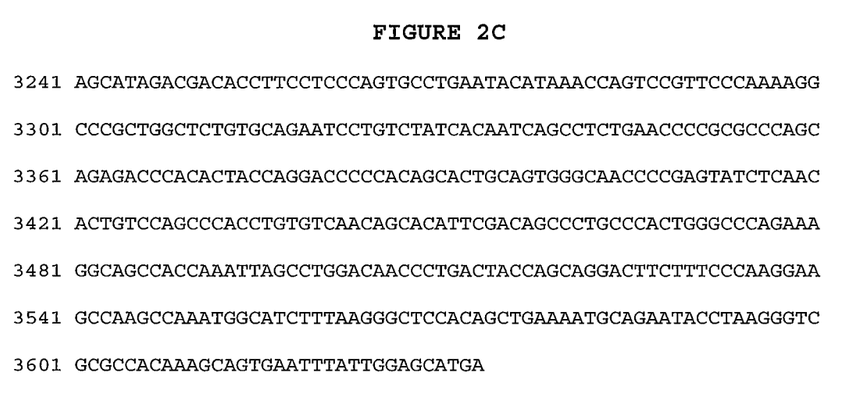

This mutation results from the nucleotide change 2573 T->G in the wild-type EGFR gene (SEQ ID NO: 1). Primers and probes for detecting both the wild-type and mutant EGFR gene (SEQ ID NO: 2) are shown in Table 1. One primer in each amplification primer pair is matched to the mutant variant and mismatched to the wild-type variant at the 3'-terminus. The remaining primer and probe are common to both mutant and wild-type target.

TABLE 1

| SEQ ID NO: 3 | GCACCCAGCAGTTTGGCC<u>A</u> | Wild-type primer |
|---|---|---|
| SEQ ID NO :4 | GCGCCCAGCAGTTTGGCC<u>C</u> | Mutant primer |
| SEQ ID NO :5 | GCGCCCAGCAGTTTGGCC<u>J</u> | Mutant primer<br>J = G-clamp |
| SEQ ID NO: 6 | GCGCCCAGCAGTTTGGCJ<u>C</u> | Mutant primer<br>J = G-clamp |
| SEQ ID NO :7 | GCGCCCAGCAGTTTGGJC<u>C</u> | Mutant primer<br>J = G-Clamp |
| SEQ ID NO :8 | GTCTTCTCTGTTTCAGGGCATGAAC | Common primer |
| SEQ ID NO :9 | FTACTGGTGAAQAACACCGCAGCATGTP | Probe: F = threo-FAM,<br>Q = BHQ-2, P = phosphate |
| SEQ ID NO: 10 | ATGTCAAGATCACAGATTTTGGGC<u>T</u> | Wild-type primer |

TABLE 1-continued

| SEQ ID NO: 11 | ATGTCAAGATCACAGATTTTGGGCG | Mutant primer |
| --- | --- | --- |
| SEQ ID NO: 12 | ATGTCAAGATCACAGATTTTGGGJG | Mutant primer J = G-clamp |
| SEQ ID NO: 13 | CTGGTCCCTGGTGTCAGGAAAA | Common primer |
| SEQ ID NO: 14 | FTACCATGCAGQAAGGAGGCAAAGTAAGGAGP | Probe: F = FAM, Q = BHQ-2, P = phosphate |

For each amplification reaction, wild-type genomic DNA (K562) was present at 10^4 copies per reaction. Linearized mutant plasmid DNA was also present at 10^4 copies per reaction. Mutant plasmids were prepared by 500 bp insertion into a pUC19 vector (provided as Minigenes from IDT; SEQ ID NOS: 15 and 16).

Each reaction amplified 10^4 copies of either mutant or wild-type target (at 10^4 copies input). The matched variant was a plasmid DNA with the insert incorporating EGFR L858R mutant sequence while the mismatched variant was the K562 gDNA. The matched primers are either non-modified or G-Clamp modified at the 3' terminus or at positions N-1 or N-2 from the 3'-terminus.

Each 12 !lL reaction contained 2.98% glycerol, 50 mM Tris-HCl (pH 8.0), 80 mM KCl, 200 µM each dATP, dCTP and dGTP, 400 µM dUTP, 0.2 µM of forward primer 0.2 µM reverse primer, 0.05 µM detection probe, 2.5% DMSO, 0.02% Pierce Tween 20, 0.036% Sodium Azide, 0.1 mM EDTA, 0.2 U/µL uracil-N-glycosylase (UNG), 200 nM NTQ21-46A aptamer, 40 nM Z05 mutant polymerase, and 2.5 mM magnesium acetate (with 0.09% sodium azide).

Amplification and analysis were done using the Roche LightCycler 480 instrument. The reactions were subjected to the following temperature profile: 50° C. for 5 minutes (UNG step) followed by 2 cycles of 95° C. for 10 seconds and 62° C. for 30 seconds and 60 cycles of 93° C. for 10 seconds and 62° C. for 30 seconds. Fluorescence data was collected at the end of each 62° C. step within the last 60 cycles.

The results of one experiment are shown on Table 2. The amplification results are expressed as a change in fluorescence in the 450-500 nm or 540-580 nm wavelength interval. The selectivity of the amplification is measured by the difference in the Ct value (ΔCt) between the matched and the mismatched targets. ΔCt for each experiment is indicated on Table 2. The data shows that the matched (mutant) variant of the target was amplified selectively over the mismatched (wild-type) variant. The selectivity was enhanced by the G-clamp modification of the nucleotides in the primer.

TABLE 2

| Primer | Average L858R Ct | Average WT Ct | ΔCt (WT − L858R) |
| --- | --- | --- | --- |
| SEQ ID NO: 3 | 36.7 | 21.6 | −15.1 |
| SEQ ID NO: 4 | 22.1 | 24.3 | 2.2 |
| SEQ ID NO: 5 | 23.8 | 26.2 | 2.4 |
| SEQ ID NO: 6 | 22.5 | 26.6 | 4.1 |
| SEQ ID NO: 7 | 22.5 | 29.4 | 6.9 |

Example 2

Primers for Detecting Mutations at the PIK3CA Gene

One primer in each amplification primer pair is matched to the mutant variant and mismatched to the wild-type variant at the 3' terminus. The remaining primer and the probe are common to both mutant and wild-type target. Wild-type genomic DNA (K562) present at 10^4 copies per reaction. Linearized mutant plasmid DNA present at 10^4 copies per reaction. Mutant plasmids were prepared by 500bp insertion into a pUC19 vector (provided as Minigenes from IDT).

The primers are non-modified or G-Clamp modified at any base position from N-1 to N-2. In some designs, an additional mismatch is introduced in the primer sequence either at or near the G-Clamp modification site.

Each 12 µL reaction contained 2.98% glycerol, 50 mM Tris-HCl (pH 8.0), 80 mM KCl, 200 µM each dATP, dCTP and dGTP, 400 µM dUTP, 0.1 µM of forward primer 0.1 µM reverse primer, 0.05 µM detection probe, 2.5% DMSO, 0.02% Pierce Tween 20, 0.036% Sodium Azide, 0.1 mM EDTA, 0.2 U/µL uracil-N-glycosylase (UNG), 200 nM NTQ21-46A aptamer, 40 nM Z05 mutant polymerase, and 2.5 mM magnesium acetate (with 0.09% sodium azide).

Amplification and analysis were done using the Roche LightCycler 480 instrument. The reactions were subjected to the following temperature profile: 50° C. for 5 minutes (UNG step) followed by 2 cycles of 95° C. for 10 seconds and 62° C. for 30 seconds and 60 cycles of 93° C. for 10 seconds and 62° C. for 30 seconds. Fluorescence data was collected at the end of each 62° C. step within the last 60 cycles.

The results of one experiment are shown on Table 3. The amplification results are expressed as a change in fluorescence in the 450-500 nm or 540-580 nm wavelength interval. The selectivity of the amplification is measured by the difference in the Ct value (ΔCt) between the matched and the mismatched targets. ΔCt for each experiment is indicated on Table 3. The data shows that for the unmodified mutant primer, the matched (mutant) variant of the target was amplified selectively over the mismatched (wild-type) variant. The selectivity was enhanced by the G-clamp modification of the nucleotides in the mutant primer.

TABLE 3

| | Average Mutant Ct | Average WT Ct | ΔCt (WT − Mutant) |
| --- | --- | --- | --- |
| Wild-type primer | 24.5 | 21.2 | −3.3 |
| Mutant primer unmodified | 22.6 | 33.6 | 11.0 |
| Mutant primer G-clamp | 27.6 | 51.5 | 23.9 |

The invention claimed is:

1. A method of allele-specific amplification of a variant of a target sequence, the target existing in the form of several variant sequences, the method comprising:
   (a) hybridizing a first and a second oligonucleotides to at least one variant of the target sequence; wherein the first oligonucleotide is at least partially complementary to one or more variants of the target sequence, and the second oligonucleotide is at least partially complementary to one or more variants of the target sequence, and has at least one selective nucleotide at the 3' terminal nucleotide that is complementary to only one variant of the target sequence; wherein said second oligonucleotide incorporates at least one G-clamp nucleotide at a position between 1 and 5 nucleotide upstream of the 3' terminal nucleotide;
   (b) extending the second oligonucleotide with a nucleic acid polymerase, wherein said polymerase is capable of extending said second oligonucleotide efficiently when said second oligonucleotide is hybridized to a variant of the target sequence which is complementary to the one selective nucleotide at the 3' terminus, and substantially less efficiently when said second oligonucleotide is hybridized to a variant of the target sequence which is not complementary to the one selective nucleotide at the 3' terminus.

2. The method of claim 1, further comprising a step (c) of detecting the product of primer extension of step (b).

3. The method of claim 1, wherein said nucleic acid polymerase is selected from a group consisting of Taq DNA polymerase, Z05 DNA polymerase, ΔZ05 DNA polymerase and ΔZ05-Gold DNA polymerase.

4. The method of claim 1 wherein said nucleic acid polymerase possesses 3'-5' nuclease activity.

5. The method of claim 4, wherein said nucleic acid polymerase is selected from a group consisting of Pfu DNA polymerase and Thermatoga Maritima.

6. The method of claim 1, wherein said variant of the sequence in step (a) is a mutation of the human PIK3CA or EGFR gene.

7. The method of claim 1, wherein said second oligonucleotide is selected from a group consisting of SEQ ID NO: 6, 7, and 12.

8. An oligonucleotide for performing an allele-specific amplification of a target sequence, said target existing in the form of several variant sequences, the oligonucleotide comprising
   (a) a sequence at least partially complementary to a portion of one or more variants of said target sequence;
   (b) one selective nucleotide at the 3' terminal nucleotide that is complementary to only one variant of the target sequence; and
   (c) at least one G-clamp nucleotide at a position between 1 and 5 nucleotides upstream of the 3' terminal nucleotide.

9. The oligonucleotide of claim 8 with a sequence selected from a group consisting of SEQ ID NO: 6, 7 and 12.

* * * * *

SEQUENCE LISTING

<160> NUMBER OF SEQ ID NOS: 16

<210> SEQ ID NO 1
<211> LENGTH: 3633
<212> TYPE: DNA
<213> ORGANISM: Homo sapiens
<220> FEATURE:
<221> NAME/KEY: misc_feature
<223> OTHER INFORMATION: EGFR wild-type gene

<400> SEQUENCE: 1

| | | | | | |
|---|---|---|---|---|---|
| atgcgaccct | ccgggacggc | cggggcagcg | ctcctggcgc | tgctggctgc | gctctgcccg | 60 |
| gcgagtcggg | ctctggagga | aaagaaagtt | tgccaaggca | cgagtaacaa | gctcacgcag | 120 |
| ttgggcactt | ttgaagatca | ttttctcagc | ctccagagga | tgttcaataa | ctgtgaggtg | 180 |
| gtccttggga | atttggaaat | tacctatgtg | cagaggaatt | atgatctttc | cttcttaaag | 240 |
| accatccagg | aggtggctgg | ttatgtcctc | attgccctca | acacagtgga | gcgaattcct | 300 |
| ttggaaaacc | tgcagatcat | cagaggaaat | atgtactacg | aaaattccta | tgccttagca | 360 |
| gtcttatcta | actatgatgc | aaataaaacc | ggactgaagg | agctgcccat | gagaaattta | 420 |
| caggaaatcc | tgcatggcgc | cgtgcggttc | agcaacaacc | ctgccctgtg | caacgtggag | 480 |
| agcatccagt | ggcgggacat | agtcagcagt | gactttctca | gcaacatgtc | gatggacttc | 540 |
| cagaaccacc | tgggcagctg | ccaaaagtgt | gatccaagct | gtccaatgg | agctgctgg | 600 |
| ggtgcaggag | aggagaactg | ccagaaactg | accaaaatca | tctgtgccca | gcagtgctcc | 660 |
| gggcgctgcc | gtggcaagtc | ccccagtgac | tgctgccaca | accagtgtgc | tgcaggctgc | 720 |
| acaggccccc | gggagagcga | ctgcctggtc | tgccgcaaat | tccgagacga | agccacgtgc | 780 |
| aaggacacct | gccccccact | catgctctac | aaccccacca | cgtaccagat | ggatgtgaac | 840 |
| cccgagggca | aatacagctt | tggtgccacc | tgcgtgaaga | agtgtccccg | taattatgtg | 900 |
| gtgacagatc | acggctcgtg | cgtccgagcc | tgtggggccg | acagctatga | gatggaggaa | 960 |
| gacggcgtcc | gcaagtgtaa | gaagtgcgaa | gggccttgcc | gcaaagtgtg | taacggaata | 1020 |
| ggtattggtg | aatttaaaga | ctcactctcc | ataaatgcta | cgaatattaa | acacttcaaa | 1080 |
| aactgcacct | ccatcagtgg | cgatctccac | atcctgccgg | tggcatttag | gggtgactcc | 1140 |
| ttcacacata | ctcctcctct | ggatccacag | gaactggata | ttctgaaaac | cgtaaaggaa | 1200 |
| atcacagggt | ttttgctgat | tcaggcttgg | cctgaaaaca | ggacggacct | ccatgccttt | 1260 |
| gagaacctag | aaatcatacg | cggcaggacc | aagcaacatg | gtcagttttc | tcttgcagtc | 1320 |
| gtcagcctga | acataacatc | cttgggatta | cgctccctca | aggagataag | tgatggagat | 1380 |
| gtgataattt | caggaaacaa | aaatttgtgc | tatgcaaata | caataaactg | gaaaaaactg | 1440 |
| tttgggacct | ccggtcagaa | aaccaaaatt | ataagcaaca | gaggtgaaaa | cagctgcaag | 1500 |
| gccacaggcc | aggtctgcca | tgccttgtgc | tcccccgagg | gctgctgggg | cccggagccc | 1560 |
| agggactgcg | tctcttgccg | gaatgtcagc | cgaggcaggg | aatgcgtgga | caagtgcaac | 1620 |
| cttctggagg | gtgagccaag | ggagtttgtg | gagaactctg | agtgcataca | gtgccaccca | 1680 |
| gagtgcctgc | ctcaggccat | gaacatcacc | tgcacaggac | ggggaccaga | caactgtatc | 1740 |
| cagtgtgccc | actacattga | cggccccac | tgcgtcaaga | cctgcccggc | aggagtcatg | 1800 |
| ggagaaaaca | acaccctggt | ctggaagtac | gcagacgccg | ccatgtgtg | ccacctgtgc | 1860 |
| catccaaact | gcacctacgg | atgcactggg | ccaggtcttg | aaggctgtcc | aacgaatggg | 1920 |
| cctaagatcc | cgtccatcgc | cactgggatg | gtgggggccc | tcctcttgct | gctggtggtg | 1980 |

```
gccctgggga tcggcctctt catgcgaagg cgccacatcg ttcggaagcg cacgctgcgg    2040
aggctgctgc aggagaggga gcttgtggag cctcttacac ccagtggaga agctcccaac    2100
caagctctct tgaggatctt gaaggaaact gaattcaaaa agatcaaagt gctgggctcc    2160
ggtgcgttcg gcacggtgta aagggactc tggatcccag aaggtgagaa agttaaaatt     2220
cccgtcgcta tcaaggaatt aagagaagca acatctccga aagccaacaa ggaaatcctc    2280
gatgaagcct acgtgatggc cagcgtggac aaccccacg tgtgccgcct gctgggcatc     2340
tgcctcacct ccaccgtgca gctcatcacg cagctcatgc ccttcggctg cctcctggac    2400
tatgtccggg aacacaaaga caatattggc tcccagtacc tgctcaactg gtgtgtgcag    2460
atcgcaaagg gcatgaacta cttggaggac cgtcgcttgg tgcaccgcga cctggcagcc    2520
aggaacgtac tggtgaaaac accgcagcat gtcaagatca cagattttgg gctggccaaa    2580
ctgctgggtg cggaagagaa agaataccat gcagaaggag gcaaagtgcc tatcaagtgg    2640
atggcattgg aatcaatttt acacagaatc tatacccacc agagtgatgt ctggagctac    2700
ggggtgactg tttgggagtt gatgaccttt ggatccaagc catatgacgg aatccctgcc    2760
agcgagatct cctccatcct ggagaaagga gaacgcctcc ctcagccacc catatgtacc    2820
atcgatgtct acatgatcat ggtcaagtgc tggatgatag acgcagatag tcgcccaaag    2880
ttccgtgagt tgatcatcga attctccaaa atggcccgag accccagcg ctaccttgtc     2940 attcaggggg atgaaagaat gcatttgcca agtcctacag actccaactt ctaccgtgcc    3000
ctgatggatg aagaagacat ggacgacgtg gtggatgccg acgagtacct catcccacag    3060
cagggcttct tcagcagccc ctccacgtca cggactcccc tcctgagctc tctgagtgca    3120
accagcaaca attccaccgt ggcttgcatt gatagaaatg ggctgcaaag ctgtcccatc    3180
aaggaagaca gcttcttgca gcgatacagc tcagacccca caggcgcctt gactgaggac    3240
agcatagacg acaccttcct cccagtgcct gaatacataa accagtccgt tcccaaaagg    3300
cccgctggct ctgtgcagaa tcctgtctat cacaatcagc ctctgaaccc cgcgcccagc    3360
agagacccac actaccagga ccccacagc actgcagtgg caaccccga gtatctcaac     3420 actgtccagc ccacctgtgt caacagcaca ttcgacagcc ctgcccactg ggcccagaaa    3480
ggcagccacc aaattagcct ggacaaccct gactaccagc aggacttctt tcccaaggaa    3540
gccaagccaa atggcatctt taagggctcc acagctgaaa atgcagaata cctaagggtc    3600
gcgccacaaa gcagtgaatt tattggagca tga                                 3633
```

<210> SEQ ID NO 2
<211> LENGTH: 3633
<212> TYPE: DNA
<213> ORGANISM: Homo sapiens
<220> FEATURE:
<221> NAME/KEY: misc_feature
<223> OTHER INFORMATION: EGFR 2573 T>G mutant gene

<400> SEQUENCE: 2

```
atgcgaccct ccgggacggc cggggcagcg ctcctggcgc tgctggctgc gctctgcccg     60
gcgagtcggg ctctggagga aaagaaagtt tgccaaggca cgagtaacaa gctcacgcag    120
ttgggcactt ttgaagatca ttttctcagc ctccagagga tgttcaataa ctgtgaggtg    180
gtccttggga atttggaaat tacctatgtg cagaggaatt atgatctttc cttcttaaag    240
accatccagg aggtggctgg ttatgtcctc attgccctca acacagtgga gcgaattcct    300
ttggaaaacc tgcagatcat cagaggaaat atgtactacg aaaattccta tgccttagca    360
```

```
gtcttatcta actatgatgc aaataaaacc ggactgaagg agctgcccat gagaaattta    420
caggaaatcc tgcatggcgc cgtgcggttc agcaacaacc ctgccctgtg caacgtggag    480
agcatccagt ggcgggacat agtcagcagt gactttctca gcaacatgtc gatggacttc    540
cagaaccacc tgggcagctg ccaaaagtgt gatccaagct gtcccaatgg gagctgctgg    600
ggtgcaggag aggagaactg ccagaaactg accaaaatca tctgtgccca gcagtgctcc    660
gggcgctgcc gtggcaagtc ccccagtgac tgctgccaca accagtgtgc tgcaggctgc    720
acaggccccc gggagagcga ctgcctggtc tgccgcaaat ccgagacga agccacgtgc    780 aaggacacct gccccccact catgctctac aaccccacca cgtaccagat ggatgtgaac    840
cccgagggca atacagcttt tggtgccacc tgcgtgaaga agtgtcccg taattatgtg    900 gtgacagatc acggctcgtg cgtccgagcc tgtgggggccg acagctatga gatggaggaa    960
gacggcgtcc gcaagtgtaa gaagtgcgaa gggccttgcc gcaaagtgtg taacggaata   1020
ggtattggtg aatttaaaga ctcactctcc ataaatgcta cgaatattaa acacttcaaa   1080
aactgcacct ccatcagtgg cgatctccac atcctgccgg tggcatttag gggtgactcc   1140
ttcacacata ctcctcctct ggatccacag gaactggata ttctgaaaac cgtaaaggaa   1200
atcacagggt ttttgctgat tcaggcttgg cctgaaaaca ggacggacct ccatgccttt   1260
gagaacctag aaatcatacg cggcaggacc aagcaacatg gtcagttttc tcttgcagtc   1320
gtcagcctga acataacatc cttgggatta cgctccctca aggagataag tgatggagat   1380
gtgataattt caggaaacaa aaatttgtgc tatgcaaata caataaactg gaaaaaactg   1440
tttgggacct ccggtcagaa aaccaaaatt ataagcaaca gaggtgaaaa cagctgcaag   1500
gccacaggcc aggtctgcca tgccttgtgc tcccccgagg ctgctgggg cccggagccc   1560 agggactgcg tctcttgccg gaatgtcagc cgaggcaggg aatgcgtgga caagtgcaac   1620
cttctggagg gtgagccaag ggagtttgtg gagaactctg agtgcataca gtgccaccca   1680
gagtgcctgc ctcaggccat gaacatcacc tgcacaggac ggggaccaga caactgtatc   1740
cagtgtgccc actacattga cggcccccac tgcgtcaaga cctgccccgc aggagtcatg   1800
ggagaaaaca cacccctggt ctggaagtac gcagacgccg gccatgtgtg ccacctgtgc   1860
catccaaact gcacctacgg atgcactggg ccaggtcttg aaggctgtcc aacgaatggg   1920
cctaagatcc cgtccatcgc cactgggatg gtgggggccc tcctcttgct gctggtggtg   1980
gccctgggga tcggcctctt catgcgaagg cgccacatcg ttcggaagcg cacgctgcgg   2040
aggctgctgc aggagaggga gcttgtggag cctcttacac ccagtggaga agctcccaac   2100
caagctctct tgaggatctt gaaggaaact gaattcaaaa agatcaaagt gctgggctcc   2160
ggtgcgttcg gcacggtgta taagggactc tggatcccag aaggtgagaa agttaaaatt   2220
cccgtcgcta tcaaggaatt aagagaagca acatctccga aagccaacaa ggaaatcctc   2280
gatgaagcct acgtgatggc cagcgtggac aaccccacg tgtgccgcct gctgggcatc   2340
tgcctcacct ccaccgtgca gctcatcacg cagctcatgc ccttcggctg cctcctggac   2400
tatgtccggg aacacaaaga caatattggc tcccagtacc tgctcaactg gtgtgtgcag   2460
atcgcaaagg gcatgaacta cttggaggac cgtcgcttgg tgcaccgcga cctggcagcc   2520
aggaacgtac tggtgaaaac accgcagcat gtcaagatca cagattttgg gcgggccaaa   2580
ctgctgggtg cggaagagaa agaataccat gcagaaggag gcaaagtgcc tatcaagtgg   2640
atggcattgg aatcaatttt acacagaatc tatacccacc agagtgatgt ctggagctac   2700
ggggtgactg tttgggagtt gatgacctt ggatccaagc catatgacgg aatccctgcc   2760
```

```
agcgagatct cctccatcct ggagaaagga gaacgcctcc ctcagccacc catatgtacc    2820
atcgatgtct acatgatcat ggtcaagtgc tggatgatag acgcagatag tcgcccaaag    2880
ttccgtgagt tgatcatcga attctccaaa atggcccgag accccagcg ctaccttgtc     2940 attcaggggg atgaaagaat gcatttgcca agtcctacag actccaactt ctaccgtgcc    3000
ctgatggatg aagaagacat ggacgacgtg gtggatgccg acgagtacct catcccacag    3060
cagggcttct tcagcagccc ctccacgtca cggactcccc tcctgagctc tctgagtgca    3120
accagcaaca attccaccgt ggcttgcatt gatagaaatg ggctgcaaag ctgtcccatc    3180
aaggaagaca gcttcttgca gcgatacagc tcagacccca caggcgcctt gactgaggac    3240
agcatagacg acaccttcct cccagtgcct gaatacataa accagtccgt tcccaaaagg    3300
cccgctggct ctgtgcagaa tcctgtctat cacaatcagc ctctgaaccc cgcgcccagc    3360
agagacccac actaccagga cccccacagc actgcagtgg caaccccga gtatctcaac     3420 actgtccagc ccacctgtgt caacagcaca ttcgacagcc ctgcccactg ggcccagaaa    3480
ggcagccacc aaattagcct ggacaaccct gactaccagc aggacttctt tcccaaggaa    3540
gccaagccaa atggcatctt taagggctcc acagctgaaa atgcagaata cctaagggtc    3600
gcgccacaaa gcagtgaatt tattggagca tga                                3633
```

<210> SEQ ID NO 3
<211> LENGTH: 19
<212> TYPE: DNA
<213> ORGANISM: Artificial sequence
<220> FEATURE:
<223> OTHER INFORMATION: Wild-type primer

<400> SEQUENCE: 3
gcacccagca gtttggcca                                                19

<210> SEQ ID NO 4
<211> LENGTH: 19
<212> TYPE: DNA
<213> ORGANISM: Artificial sequence
<220> FEATURE:
<223> OTHER INFORMATION: mutant primer

<400> SEQUENCE: 4
gcgcccagca gtttggccc                                                19

<210> SEQ ID NO 5
<211> LENGTH: 19
<212> TYPE: DNA
<213> ORGANISM: Artificial sequence
<220> FEATURE:
<223> OTHER INFORMATION: mutant primer
<220> FEATURE:
<221> NAME/KEY: modified_base
<222> LOCATION: (19)..(19)
<223> OTHER INFORMATION: G-clamp

<400> SEQUENCE: 5
gcgcccagca gtttggccc                                                19

<210> SEQ ID NO 6
<211> LENGTH: 19
<212> TYPE: DNA
<213> ORGANISM: Artificial sequence
<220> FEATURE:
<223> OTHER INFORMATION: mutant primer
<220> FEATURE:

```
<221> NAME/KEY: modified_base
<222> LOCATION: (18)..(18)
<223> OTHER INFORMATION: G-clamp

<400> SEQUENCE: 6
gcgcccagca gtttggccc                                                   19

<210> SEQ ID NO 7
<211> LENGTH: 19
<212> TYPE: DNA
<213> ORGANISM: Artificial sequence
<220> FEATURE:
<223> OTHER INFORMATION: mutant primer
<220> FEATURE:
<221> NAME/KEY: modified_base
<222> LOCATION: (17)..(17)
<223> OTHER INFORMATION: G-clamp

<400> SEQUENCE: 7
gcgcccagca gtttggccc                                                   19

<210> SEQ ID NO 8
<211> LENGTH: 25
<212> TYPE: DNA
<213> ORGANISM: Artificial sequence
<220> FEATURE:
<223> OTHER INFORMATION: common primer

<400> SEQUENCE: 8
gtcttctctg tttcagggca tgaac                                            25

<210> SEQ ID NO 9
<211> LENGTH: 25
<212> TYPE: DNA
<213> ORGANISM: Artificial sequence
<220> FEATURE:
<223> OTHER INFORMATION: probe

<400> SEQUENCE: 9
tactggtgaa aacaccgcag catgt                                            25

<210> SEQ ID NO 10
<211> LENGTH: 25
<212> TYPE: DNA
<213> ORGANISM: Artificial sequence
<220> FEATURE:
<223> OTHER INFORMATION: wild-type primer

<400> SEQUENCE: 10
atgtcaagat cacagatttt gggct                                            25

<210> SEQ ID NO 11
<211> LENGTH: 25
<212> TYPE: DNA
<213> ORGANISM: Artificial sequence
<220> FEATURE:
<223> OTHER INFORMATION: mutant primer

<400> SEQUENCE: 11
atgtcaagat cacagatttt gggcg                                            25

<210> SEQ ID NO 12
<211> LENGTH: 25
<212> TYPE: DNA
<213> ORGANISM: Artificial sequence
<220> FEATURE:
<223> OTHER INFORMATION: mutant primer
```

```
<220> FEATURE:
<221> NAME/KEY: modified_base
<222> LOCATION: (24)..(24)
<223> OTHER INFORMATION: G-clamp

<400> SEQUENCE: 12
atgtcaagat cacagatttt gggcg                                          25

<210> SEQ ID NO 13
<211> LENGTH: 22
<212> TYPE: DNA
<213> ORGANISM: Artificial sequence
<220> FEATURE:
<223> OTHER INFORMATION: common primer

<400> SEQUENCE: 13
ctggtccctg gtgtcaggaa aa                                             22

<210> SEQ ID NO 14
<211> LENGTH: 29
<212> TYPE: DNA
<213> ORGANISM: Artificial sequence
<220> FEATURE:
<223> OTHER INFORMATION: probe

<400> SEQUENCE: 14
taccatgcag aaggaggcaa agtaaggag                                      29

<210> SEQ ID NO 15
<211> LENGTH: 500
<212> TYPE: DNA
<213> ORGANISM: Homo sapiens
<220> FEATURE:
<221> NAME/KEY: misc_feature
<223> OTHER INFORMATION: EGFR wild-type minigene

<400> SEQUENCE: 15
tcttctttca tgcgcctttc cattctttgg atcagtagtc actaacgttc gccagccata    60
agtcctcgac gtggagaggc tcagagcctg gcatgaacat gaccctgaat tcggatgcag  120
agcttcttcc catgatgatc tgtccctcac agcagggtct tctctgtttc agggcatgaa  180
ctacttggag gaccgtcgct tggtgcaccg cgacctggca gccaggaacg tactggtgaa  240
aacaccgcag catgtcaaga tcacagattt tgggctggcc aaaactgctg gtgcggaaga  300
gaaagaatac catgcagaag gaggcaaagt aaggaggtgg ctttaggtca gccagcattt  360
tcctgacacc agggaccagg ctgccttccc actagctgta ttgtttaaca catgcagggg  420
aggatgctct ccagacattc tgggtgagct cgcagcagct gctgctggca gctgggtcca  480
gccagggtct cctggtagtg                                                500

<210> SEQ ID NO 16
<211> LENGTH: 500
<212> TYPE: DNA
<213> ORGANISM: Homo sapiens
<220> FEATURE:
<221> NAME/KEY: misc_feature
<223> OTHER INFORMATION: EGFR 2573 T>G mutant minigene

<400> SEQUENCE: 16
tcttctttca tgcgcctttc cattctttgg atcagtagtc actaacgttc gccagccata    60
agtcctcgac gtggagaggc tcagagcctg gcatgaacat gaccctgaat tcggatgcag  120
agcttcttcc catgatgatc tgtccctcac agcagggtct tctctgtttc agggcatgaa  180
```

```
ctacttggag gaccgtcgct tggtgcaccg cgacctggca gccaggaacg tactggtgaa    240
aacaccgcag catgtcaaga tcacagattt tgggcgggcc aaactgctgg gtgcggaaga    300
gaaagaatac catgcagaag gaggcaaagt aaggaggtgg ctttaggtca gccagcattt    360
tcctgacacc agggaccagg ctgccttccc actagctgta ttgtttaaca catgcagggg    420
aggatgctct ccagacattc tgggtgagct cgcagcagct gctgctggca gctgggtcca    480
gccagggtct cctggtagtg                                                 500
```